US008103017B2

(12) United States Patent
Nakagaki

(10) Patent No.: US 8,103,017 B2
(45) Date of Patent: Jan. 24, 2012

(54) SOUND REPRODUCING SYSTEM AND AUTOMOBILE USING SUCH SOUND REPRODUCING SYSTEM

(75) Inventor: Toshiya Nakagaki, Osaka (JP)

(73) Assignee: Panasonic Corporation, Osaka (JP)

( * ) Notice: Subject to any disclaimer, the term of this patent is extended or adjusted under 35 U.S.C. 154(b) by 1237 days.

(21) Appl. No.: 11/630,106

(22) PCT Filed: Apr. 14, 2006

(86) PCT No.: PCT/JP2006/307914
§ 371 (c)(1),
(2), (4) Date: Dec. 20, 2006

(87) PCT Pub. No.: WO2006/112382
PCT Pub. Date: Oct. 26, 2006

(65) Prior Publication Data

US 2008/0292106 A1 Nov. 27, 2008

(30) Foreign Application Priority Data

Apr. 14, 2005 (JP) ................................ 2005-116845

(51) Int. Cl.
*H04B 1/00* (2006.01)
*A61F 11/06* (2006.01)
*G10K 11/16* (2006.01)
*H03B 29/00* (2006.01)
*H04R 1/02* (2006.01)

(52) U.S. Cl. ............................ 381/86; 381/71.4; 381/89

(58) Field of Classification Search .................... 381/86, 381/71.4, 89
See application file for complete search history.

(56) References Cited

U.S. PATENT DOCUMENTS 4,594,729 A * 6/1986 Weingartner .................. 381/18
6,038,325 A 3/2000 Yoshida et al.
6,477,255 B1 11/2002 Yoshida et al.
2002/0076059 A1* 6/2002 Joynes ........................ 381/71.6
2004/0105550 A1* 6/2004 Aylward et al. ................ 381/17

FOREIGN PATENT DOCUMENTS

| | | |
|---|---|---|
| JP | 5-223334 | 8/1993 |
| JP | 5-308698 | 11/1993 |
| JP | 6-334545 | 12/1994 |
| JP | 10-224887 | 8/1998 |
| JP | 2000-59882 | 2/2000 |
| JP | 2003-47097 | 2/2003 |
| JP | 2004-080765 | 3/2004 |

* cited by examiner

*Primary Examiner* — Xu Mei
*Assistant Examiner* — Douglass Suthers
(74) *Attorney, Agent, or Firm* — Wenderoth, Lind & Ponack, L.L.P.

(57) ABSTRACT

A sound reproduction system provided for in-vehicle use includes: a music signal source; a first group of a first transducer, a second transducer, a third transducer and a fourth transducer connected to the music signal source; a signal processor shifting the phase of first sound signals output from the music signal source; and a second group of a first transducer, a second transducer, a third transducer and a fourth transducers connected to the signal processor.

4 Claims, 5 Drawing Sheets

SOUND REPRODUCING SYSTEM AND AUTOMOBILE USING SUCH SOUND REPRODUCING SYSTEM

This application is a U.S. national phase application of PCT International Application PCT/JP2006/307914, filed Apr. 14, 2006.

BACKGROUND OF THE INVENTION

1. Field of Invention

The present invention relates to a sound reproduction system and a vehicle using the same.

2. Description of the Related Art

A conventional sound reproduction system has a configuration as shown in FIG. 5. In FIG. 5, a plurality of audio files stored in memory 1 are transmitted to distribution box 2. Distribution box 2 is controlled to transmit requested audio files to respective transducers 3. Where, each transducer 3 stands for a headphone or a speaker embedded in a headrest.

Additionally, there is a technology called active noise canceling, as illustrated in FIG. 6. In FIG. 6, microphone 5 detects noises propagating in duct 4 to create a sound wave with an anti-phase to the detected sound wave by signal processor 6, allowing speaker 7 to produce the anti-phase sound wave to cancel the noises out.

Known Information Disclosure Statements (IDS) for the present patent application are for instance Unexamined Japanese Patent Publication No. 2004-80765 and No. H05-223334.

However, a problem has been that a vehicle with the conventional sound reproduction system lacks comfortable in-vehicle environment.

That is, in the conventional system, passengers in the backseat need to use a headphone to prevent a driver from hearing a loud sound, such as an explosion sound in a movie, which damages a comfortable in-vehicle environment. Even if a speaker is embedded in a headrest instead of using a headphone, the sound volume is restricted to prevent a loud sound in a movie from leaking, causing a lack in a comfortable in-vehicle environment.

BRIEF SUMMARY OF THE INVENTION

The present invention aims at solving aforementioned problems and providing a sound reproduction system to realize a comfortable in-vehicle environment.

The sound reproduction system includes: a first sound signal source; a first transducer connected to the first sound signal source; a signal processor connected to the first sound signal source for shifting a phase of a first sound signal output from the first sound signal source by 180 degrees; and a second transducer connected to the signal processor.

In a vehicle using the sound reproduction system, only the sound output from the first transducer can be canceled for a certain passenger's seat. Therefore, passengers sitting on the backseat can enjoy movies or music that they request in a loud sound from the first transducer without using any headphone. Only the sound is canceled at the driver's seat but sounds necessary to hear such as horns or the like are not canceled, which can realize a comfortable in-vehicle environment.

DETAILED DESCRIPTION OF THE INVENTION

Exemplary Embodiment 1

The sound reproduction system and a vehicle using the same used in exemplary embodiment 1 of the present invention are described with reference to the drawings.

Figure 1:
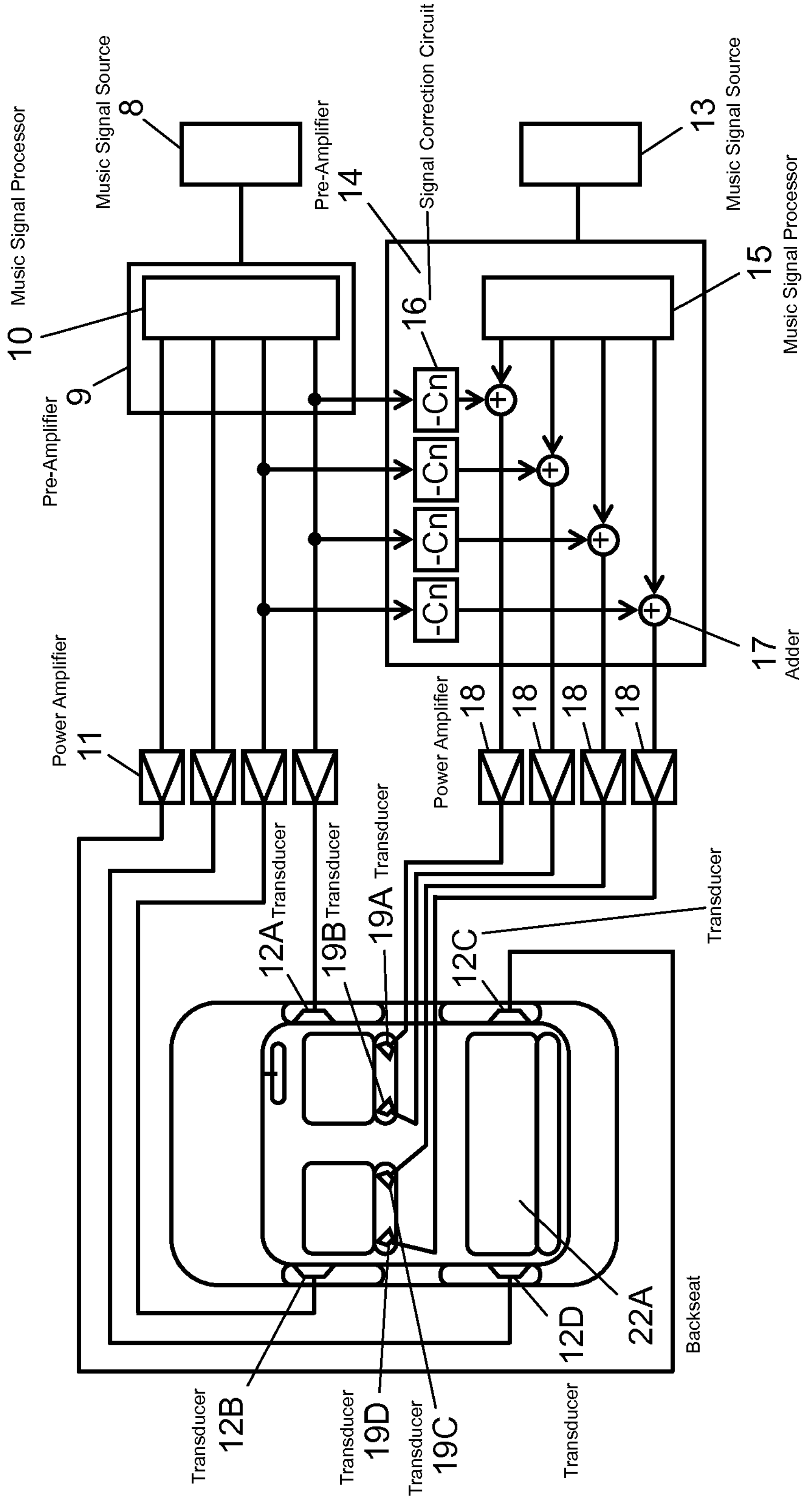
FIG. 1 shows a block diagram of a sound reproduction system and a vehicle using the same in exemplary embodiment 1 of the present invention.

FIG. 1 is a block diagram of a sound reproduction system and a vehicle using the same used in exemplary embodiment 1 of the present invention. In FIG. 1, the first music signal (first sound signal) transmitted from music signal source 8 (first sound signal source) such as a DVD or CD player is input into preamplifier 9. Subsequently, the first music signals are output as a plurality of channel signals by music signal processor 10 composed of: a signal selector, a signal mixer, an electronic volume, a bass/treble control, a fader/balance, a high-pass/low-pass filter, a fixed equalizer, a loudness control or the like (not shown in the drawing) in preamplifier 9. A case using a four-channel speaker is described in this exemplary embodiment 1, though other channel numbers could be acceptable. Music signal processor 10 is described as a digital signal processor in this exemplary embodiment 1, though an analog signal processor could be acceptable.

Channel signals output from music signal processor 10 are amplified by power amplifier 11 and are output from transducers (first transducer): 12A, 12B, 12C and 12D respectively. The transducer could be composed of a plurality of speakers or of for instance a set of speakers including a woofer and squawker in a door portion, and a tweeter in a pillar portion.

Meanwhile, second music signals output from music signal source 13 (second sound source) are input into preamplifier 14. Subsequently, the second music signals are output as a plurality of channel signals by music signal processor 15 composed of a signal selector, a signal mixer, an electronic volume, a bass/treble control, a fader/balance, a high-pass/low-pass filter, a fixed equalizer, a loudness control or the like (not shown) in preamplifier 9. Similar to the first music signal a case of using a four-channel speaker is described also in the second music signal, though the other number of channels could be acceptable for the configuration. Music signal processor 15 is described as a digital signal processor, though an analog signal processor could be acceptable.

Among channel signals output from music signal processor 10, two channel signals each directing to transducers (first transducer) 12A and 12B are input into preamplifier 14. Signal correction circuit 16 (signal processor) in preamplifier 14 shifts the phase of the channel signals by 180 degrees. However, the gain characteristics are kept unchanged. The four phase-shifted channel signals are added to the channel signals output from music signal processor 15 by adding circuit 17 (signal adder). After being added by adding circuit 17, the four channel signals are amplified in power amplifier 18 and then output from transducers (second transducer) 19A, 19B, 19C and 19D respectively.

Figure 2:
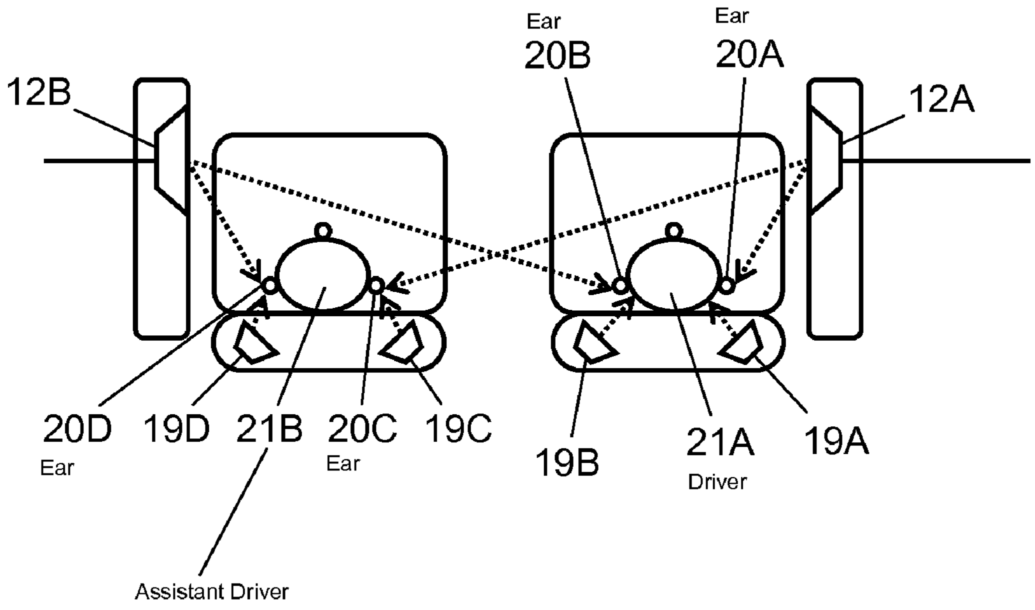
FIG. 2 shows a top view showing a positional relation between transducers of the sound reproduction system and a listener in exemplary embodiment 1 of the present invention.

FIG. 2 shows a top view showing a positional relation between transducers of the sound reproduction system and a listener in exemplary embodiment 1 of the present invention. In FIG. 2, transducers 19A and 12A have a large relational influence on a sound transmission for ear 20A. That is, the channel signal output from transducer 19A is added to a 180-degree phase-shifted channel signal of the channel signal directing to transducer 12A by adding circuit 17 in preamplifier 14 as shown in FIG. 1. As aforementioned, since the gain characteristics of the 180-degree phase-shifted signal are kept unchanged from the original signal, these two signals will cancel each other out. The output from transducer 12A will be reduced by the output from transducer 19A for ear 20A shown in FIG. 2 consequently.

Similarly, as shown in FIG. 1, the channel signal output from transducer 19B is added to a 180-degree phase-shifted channel signal of the channel signal directing to transducer 12B by adding circuit 17 in preamplifier 14. As aforementioned, since the gain characteristics of the 180-degree phase-shifted signal are kept unchanged from the original signal, these two signals will cancel each other out. The output from transducer 12B will be reduced by the output from transducer 19B for ear 20B shown in FIG. 2 consequently.

Moreover, the channel signal output from transducer 19C is added to a 180-degree phase-shifted channel signal of the channel signal directing to transducer 12A by adding circuit 17 in preamplifier 14 as shown in FIG. 1. As aforementioned, since the gain characteristics of the 180-degree phase-shifted signal are kept unchanged from the original signal, these two signals will cancel each other out. The output from transducer 12A will be reduced by the output from transducer 19C for ear 20C shown in FIG. 2 consequently.

Additionally, the channel signal output from transducer 19D is added to a 180-degree phase-shifted channel signal of the channel signal directing to transducer 12B by adding circuit 17 in preamplifier 14 as shown in FIG. 1. As aforementioned, since the gain characteristics of the 180-degree phase-shifted signal are kept unchanged from the original signal, these two signals will cancel each other out. The output from transducer 12B will be reduced by the output from transducer 19D for ear 20D as shown in FIG. 2 consequently.

Since the configuration reduces the first music signal, from the driver's seat 21A and the assistant driver's seat 21B (located in a front portion of the vehicle) it becomes harder to listen to sounds of the first music signal but easier to sounds of the second music signal. Therefore, passengers sitting on backseat 22A (located in a back portion of the vehicle) shown in FIG. 1 can see and listen to a movie in a loud sound from the first music signal source by using transducers 12A, 12B, 12C and 12D, while a comfortable in-vehicle environment is maintained without being heard the loud sound by the driver.

Moreover, with the second music signal stopped temporarily, driver 21A and assistant driver 21B may be provided with the first music signal in a reduced condition. In FIG. 2, by switching off the power supply for transducers 19C and 19D assistant driver 21B can also enjoy the output from transducers 12A, 12B, 12C and 12D.

Transducers 19A and 19B should preferably be disposed as near as possible to the driver's seat (e.g., near right and left back side portions of the driver's seat). "Near the driver's seat" means an area within one meter from the driver's ear. Transducers 19C and 19D should preferably be disposed as near as possible to the assistant driver's seat (e.g., near right and left back side portions of the assistant driver's seat). "Near the assistant driver's seat" means an area within one meter from the assistant driver's ear. Transducers 19C and 19D can be disposed not only near the assistant driver's seat but near the other passenger seat. "Near the other passenger seat" means an area within one meter from an ear of a passenger sitting on the seat.

Figure 3:
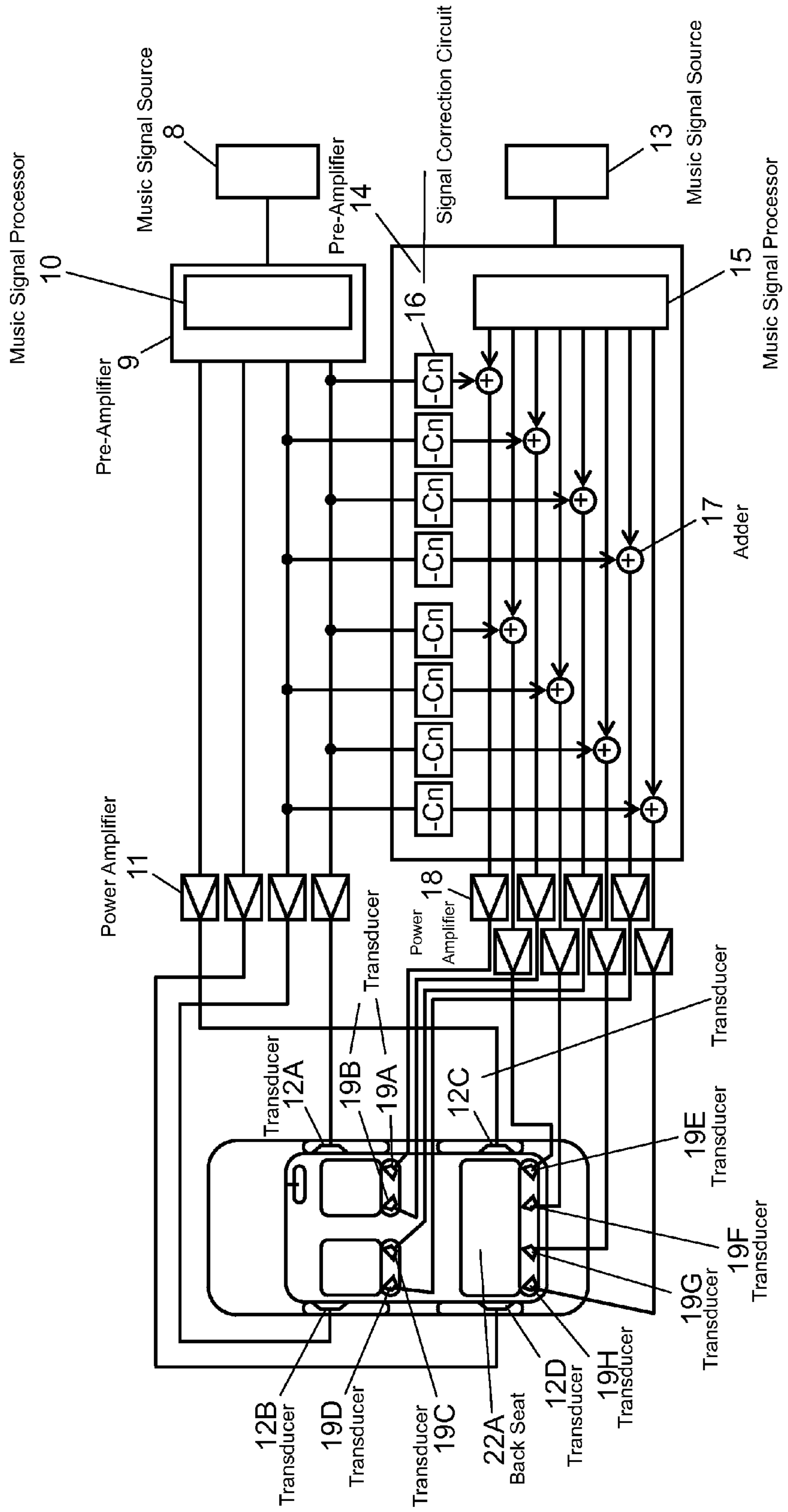
FIG. 3 shows another block diagram of a sound reproduction system and a vehicle using the same in exemplary embodiment 1 of the present invention.

FIG. 3 shows another block diagram of a sound reproduction system and a vehicle using the same in exemplary embodiment 1 of the present invention. In FIG. 3, backseat 22A is further provided with transducers 19E, 19F, 19G and 19H. Among channel signals output from music signal processor 10, two channel signals each directing to transducers 12A and 12B are input into preamplifier 14. Signal correction circuit 16 in preamplifier 14 shifts the phase of the channel signals by 180 degrees. However, the gain characteristics are kept unchanged. The four phase-shifted channel signals directing to transducers 12A and 12B are added to the channel signals output from music signal processor 15 by adding circuit 17. After being added by adding circuit 17, the four channel signals are amplified in power amplifier 18 and then output from transducers 19E, 19F, 19G and 19H, respectively.

The aforementioned configuration enables passengers to choose either of the first music signal or the second music signal which he/she likes to listen in every seat.

Exemplary Embodiment 2

The sound reproduction system and a vehicle using the same used in exemplary embodiment 2 of the present invention are described with reference to the drawings. Elements similar to those in exemplary embodiment 1 have the same reference marks and the detailed descriptions are omitted.

Figure 4:
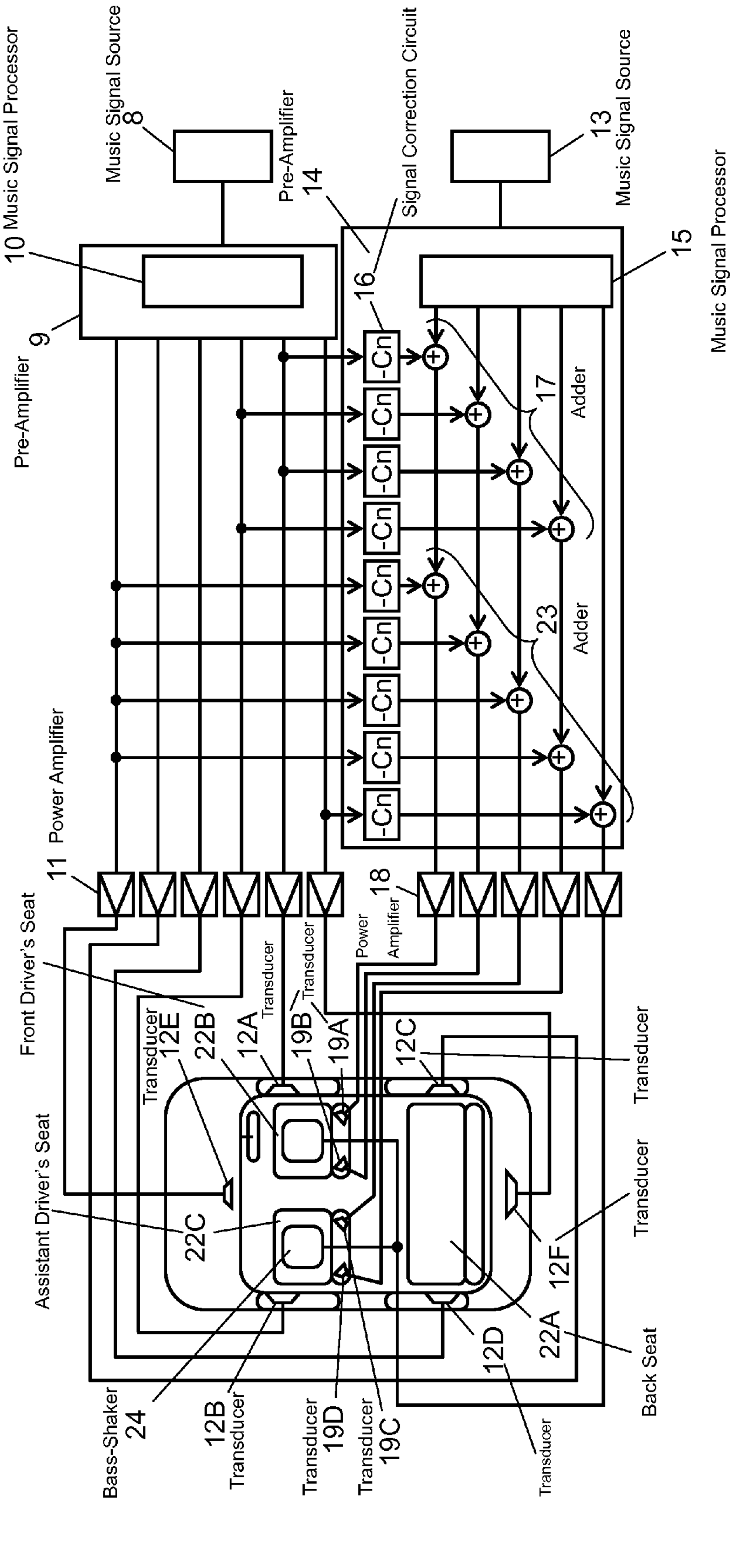
FIG. 4 shows a block diagram of a sound reproduction system and a vehicle using the same in exemplary embodiment 2 of the present invention.
Figure 5:
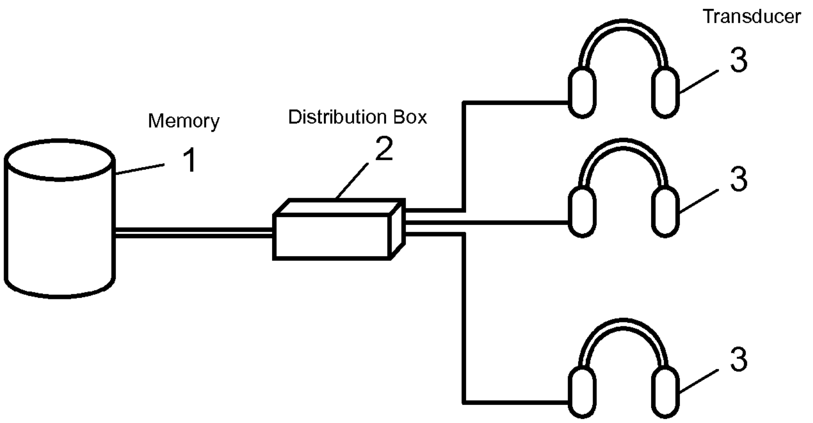
FIG. 5 Prior Art
FIG. 5 shows a view of a conventional sound reproduction system.
Figure 6:
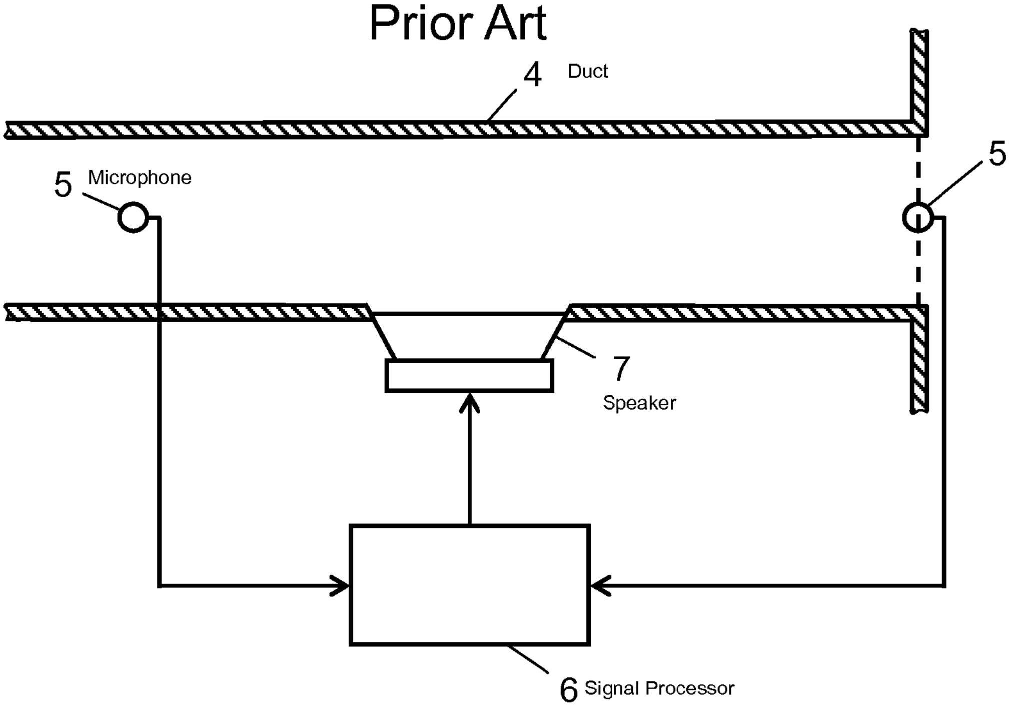
FIG. 6 Prior Art
FIG. 6 shows another view of a conventional sound reproduction system.

FIG. 4 shows a block diagram of a sound reproduction system and a vehicle using the same used in exemplary embodiment 2 of the present invention. In FIG. 4, transducer 12E is disposed in front of driver's seat 22B and transducer 12F designed to reproduce bass only is at the back of backseat 22A. Additionally, bass-shakers 24 are disposed on driver's seat 22B and on assistant driver's seat 22C.

First music signals output from music signal source 8 are input into preamplifier 9. Subsequently, the first music signals are output as a plurality of channel signals by music signal processor 10 composed of: a signal selector, a signal mixer, an electronic volume, a bass/treble control, a fader/balance, a high-pass/low-pass filter, a fixed equalizer, a loudness control or the like (not shown in the drawing) in preamplifier 9. The channel signals output from music signal processor 10 are amplified by power amplifiers 11 and are output from transducers: 12A, 12B, 12C, 12D, 12E and 12F respectively.

Meanwhile, second music signals output from music signal source 13 are input into preamplifier 14. Subsequently, the second music signals are output as a plurality of channel signals by music signal processor 15 composed of: a signal selector, a signal mixer, an electronic volume, a bass/treble control, a fader/balance, a high-pass/low-pass filter, a fixed equalizer, a loudness control or the like (not shown) in preamplifier 14.

Among the channel signals output from music signal processor 10, two channel signals each directing to transducers 12A and 12B are input into preamplifier 14. Signal correction circuit 16 in preamplifier 14 shifts the phase of the channel signals by 180 degrees. However, the gain characteristics are kept unchanged.

Similarly, among the channel signals output from music signal processor 10, four channel signals directing to transducer 12E are input into preamplifier 14. Signal correction circuit 16 in preamplifier 14 shifts the phase of the channel signals by 180 degrees. However, the gain characteristics are kept unchanged.

Four phase-shifted channel signals directing to transducers 12A and 12B, four phase-shifted channel signals directing to transducer 12E, and channel signal output from music signal processor 15 are added together by adding circuits 17 and 23. Four channel signals that have been created by adding circuits 17 and 23 are amplified in power amplifier 18 and then output from transducers 19A, 19B, 19C and 19D respectively.

Among the channel signals output from music signal processor 10, channel signals directing to transducer 12F are input into preamplifier 14. Signal correction circuit 16 in preamplifier 14 shifts the phase of the channel signals by 180 degrees. However, the gain characteristics are kept unchanged.

Phase-shifted channel signals directing to transducer 12F and channel signals output from music signal processor 15 are added together by adding circuit 23. Channel signals that have been created by adding circuit 23 are amplified in power amplifier 18 and then output from bass-shaker 24.

This can realize a configuration suitable for 5.1-ch known as the surround-sound system. At the same time, the first music signal can be reduced for driver 21A and assistant driver 21B. That is, the output from transducer 12E can be reduced by using the output from transducers 19A, 19B, 19C and 19D, and the output from transducer 12F designed to reproduce bass only can be reduced by bass-shakers 24 effectively. Therefore, passengers sitting on backseat 22A shown in FIG. 1 can see and listen to a movie in a loud sound by using transducers 12A, 12B, 12C, 12D, 12E and 12F, while a comfortable in-vehicle environment is maintained without being heard the loud sound by the driver.

Moreover, with the second music signal stopped temporarily, driver 21A and assistant driver 21B may be provided with the first music signal in a lower level condition. In FIG. 4, by switching off the power supply for transducers 19C and 19D assistant driver 21B can also enjoy the output from transducers 12A, 12B, 12C, 12D, 12E and 12F.

INDUSTRIAL APPLICABILITY

The sound reproduction system disclosed in this invention performs such that only the sound of movie or the like being listened in backseats can be canceled at the driver's seat, and that the driver can listen to other audio programs at the driver's seat, which is useful as a sound reproduction system for use in a vehicle or the like.

The invention claimed is:

1. A sound reproduction system for use in a motor vehicle, the motor vehicle including a front portion and a back portion, the front portion of the motor vehicle including a driver's seat, an assistant driver's seat, a right side and a left side, and the back portion of the motor vehicle including a right side and a left side, the sound reproduction system comprising:

a first sound signal source operable to output a first sound signal, such that a first channel signal group including four channel signals is processed from the first sound signal;

a second sound signal source operable to output a second sound signal, such that a second channel signal group including four channel signals is processed from the second sound signal;

a first transducer group including four transducers operable to output the four channel signals of the first channel signal group;

a second transducer group including four transducers operable to output the four channel signals of the second channel signal group;

a signal processor operable to shift a phase of a first channel signal and a second channel signal of the first channel signal group by 180 degrees to output four signals;

a first signal adder operable to respectively add each signal of the four signals outputted from the signal processor to a respective channel signal of the four channel signals of the second channel group, wherein a first transducer of the first transducer group is for being disposed at the right side of the front portion of the motor vehicle and is operable to output the first channel signal of the first channel signal group, wherein a second transducer of the first transducer group is for being disposed at the left side of the front portion of the motor vehicle and is operable to output the second channel signal of the first channel signal group, wherein a third transducer of the first transducer group is for being disposed at the right side of the back portion of the motor vehicle and is operable to output a third channel signal of the first channel signal group, wherein a fourth transducer of the first transducer group is for being disposed at the left side of the back portion of the motor vehicle and is operable to output a fourth channel signal of the first channel signal group, wherein a first transducer of the second transducer group is for being disposed at a right back side of the driver's seat of the motor vehicle and is operable to output a first added signal obtained by the first signal adder adding a first channel signal of the second channel signal group to the 180 degree phase shifted first channel signal of the first channel signal group shifted by the signal processor, wherein a second transducer of the second transducer group is for being disposed at a left back side of the driver's seat of the motor vehicle and is operable to output a second added signal obtained by the first signal adder adding a second channel signal of the second channel group to the 180 degree phase shifted second channel signal of the first channel signal group shifted by the signal processor, wherein a third transducer of the second transducer group is for being disposed at a right back side of the assistant driver's seat of the motor vehicle and is operable to output a third added signal obtained by the first signal adder adding a third channel signal of the second channel signal group to the 180 degree phase shifted first channel signal of the first channel signal group shifted by the signal processor, and wherein a fourth transducer of the second transducer group is for being disposed at a left back side of the assistant driver's seat of the motor vehicle and is operable to output a fourth added signal obtained by the first signal adder adding a fourth channel signal of the second channel signal group to the 180 degree phase shifted second channel signal of the first channel signal group shifted by the signal processor.

2. A vehicle including the sound reproduction system of claim 1.

3. The sound reproduction system of claim 1, further comprising:

a second signal adder; and a bass-shaker operable to reproduce a bass signal and for being disposed on the driver's seat and the assistant driver's seat, wherein the first channel signal group further includes a fifth channel signal and a sixth channel signal, wherein the second channel signal group further includes a fifth channel signal, wherein the signal processor is further operable to shift a phase of the fifth channel signal of the first channel signal group and a phase of the sixth channel signal of the first channel signal group by 180 degrees, respectively, so as to output five additional signals, wherein the second signal adder is operable to respectively add each signal of the five additional signals outputted from the signal processor to a respective channel signal of five channel signals including four signals outputted from the first signal adder and the fifth channel signal of the second channel signal group, wherein the first transducer group further includes:

a fifth transducer for being disposed in front of the driver's seat and operable to output the fifth channel signal of the first channel signal group; and a sixth transducer for being disposed at the back portion of the motor vehicle and operable to output the sixth channel signal of the first channel signal group, wherein the first transducer of the second transducer group outputs a fifth added signal obtained by the second signal adder adding the 180 degree phase shifted signal of the fifth channel signal of the first channel signal group shifted by the signal processor to the first added signal, wherein the second transducer of the second transducer group outputs a sixth added signal obtained by the second signal adder adding the 180 degree phase shifted signal of the fifth channel signal of the first channel signal group shifted by the signal processor to the second added signal, wherein the third transducer of the second transducer group outputs a seventh added signal obtained by the second signal adder adding the 180 degree phase shifted signal of the fifth channel signal of the first channel signal group shifted by the signal processor to the third added signal, wherein the fourth transducer of the second transducer group outputs an eighth added signal obtained by the second signal adder adding the 180 degree phase shifted signal of the fifth channel signal of the first channel signal group shifted by the signal processor to the fourth added signal, and wherein the bass-shaker outputs a ninth added signal obtained by the second signal adder adding the 180 degree phase shifted signal of the sixth channel signal of the first channel signal group shifted by the signal processor to the fifth channel signal of the second channel signal group.

4. A vehicle including the sound reproduction system of claim 3.

* * * * *